United States Patent [19]

Foltz et al.

[11] 4,050,528
[45] Sept. 27, 1977

[54] WIRE INSERTER

[75] Inventors: Carl L. Foltz, Holiday; Vernon H. Troutner, Petersburg; Arthur F. Trott, Largo, all of Fla.

[73] Assignee: Concept, Inc., Clearwater, Fla.

[21] Appl. No.: 623,391

[22] Filed: Oct. 17, 1975

Related U.S. Application Data

[63] Continuation-in-part of Ser. No. 610,869, Sept. 5, 1975.

[51] Int. Cl.² .......................................... A61B 17/18
[52] U.S. Cl. ............................. 173/163; 128/92 B; 173/170; 310/50
[58] Field of Search ............ 173/163, 170; 310/50; 128/92 B, 92 EB, 92 EC, 305; 320/2; 30/500, DIG. 1

[56] References Cited

U.S. PATENT DOCUMENTS

| | | | |
|---|---|---|---|
| 2,710,000 | 6/1955 | Cromer et al. | 128/305 X |
| 3,109,238 | 11/1963 | Marks | 310/50 X |
| 3,173,417 | 3/1965 | Horner | 310/50 X |
| 3,329,185 | 7/1967 | Hettich et al. | 173/163 UX |
| 3,509,629 | 5/1970 | Kidokoro et al. | 310/50 |
| 3,718,340 | 2/1973 | Stewart | 173/163 X |
| 3,734,207 | 5/1973 | Fishbein | 173/163 X |
| 3,802,518 | 4/1974 | Albert | 173/163 X |
| 3,883,789 | 5/1975 | Achenbach | 310/50 X |
| 3,905,429 | 9/1975 | Berger | 173/163 |
| 3,935,909 | 2/1976 | Mabuchi | 173/163 |

OTHER PUBLICATIONS

Assembly, Operation, Maintenance of Micro-Pneumatic K Wire Driver and Bore Drill Received 6/20/74.

*Primary Examiner*—Ernest R. Purser
*Assistant Examiner*—William F. Pate, III
*Attorney, Agent, or Firm*—Gipple & Hale

[57] ABSTRACT

A portable surgical wire inserting instrument comprising a housing defining a handle, a drive casing and a nose piece removably mounted to said drive casing. The housing handle holds a removable cassette in which is mounted a motor and a source of power electrically connected to the motor. A beveled gear extends from the cassette and is connected by a drive shaft to the motor. A wire housing tube mounted in the housing is provided with a chuck at one end adapted to grab and fixedly hold an inner chuck of a wire inserted in the wire holding tube. A beveled gear in the drive casing connects the beveled gear extending from the cassette to the wire holding tube with the gears being adapted to rotate the wire holding tube upon energization of the motor.

14 Claims, 22 Drawing Figures

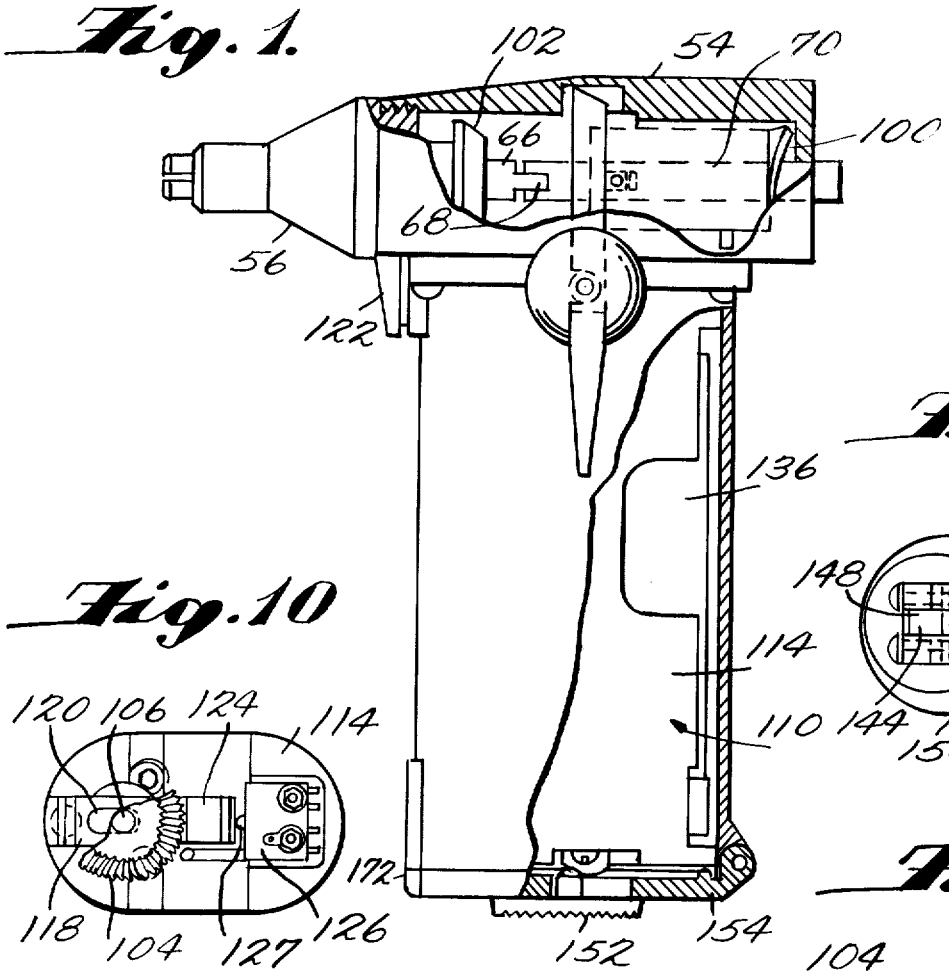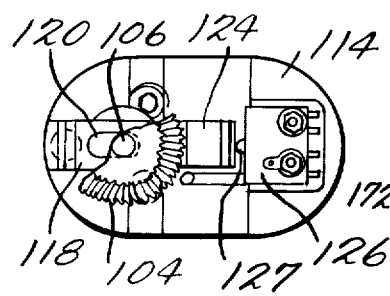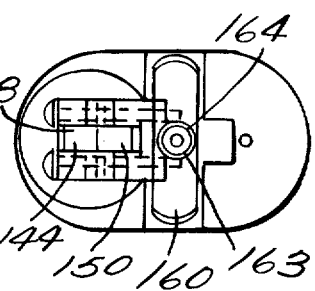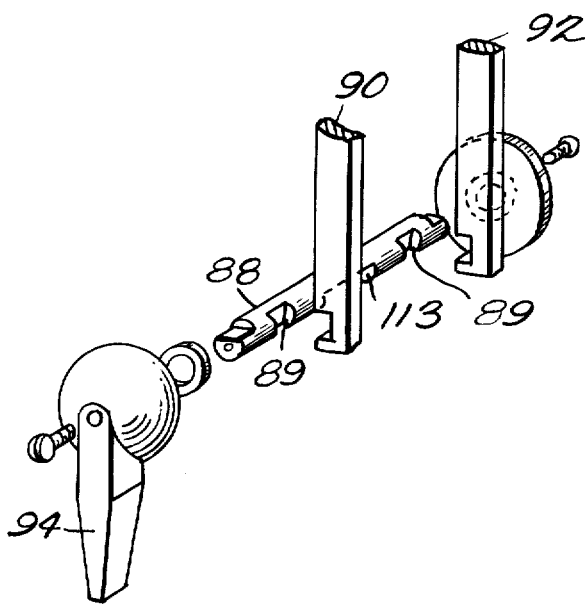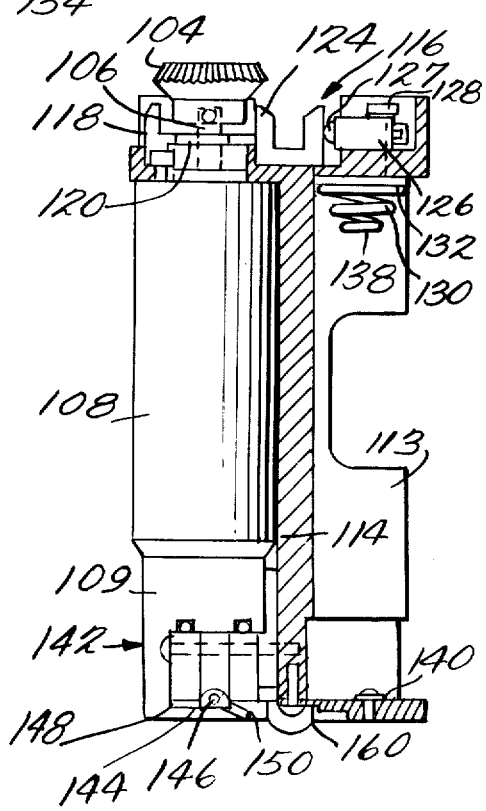

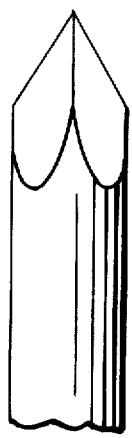
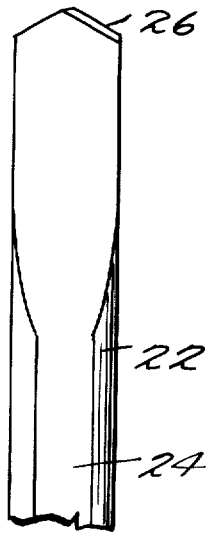
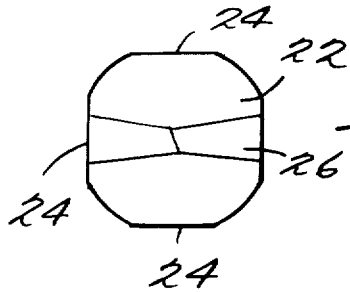
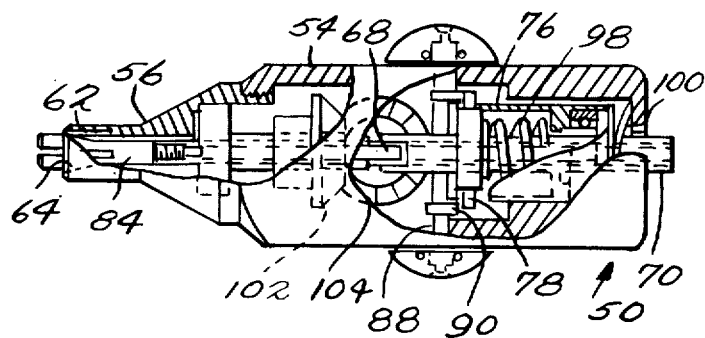

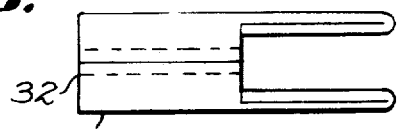
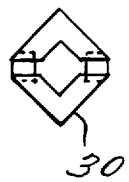
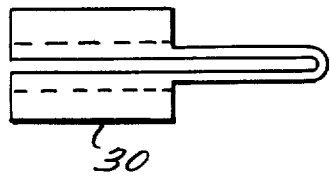
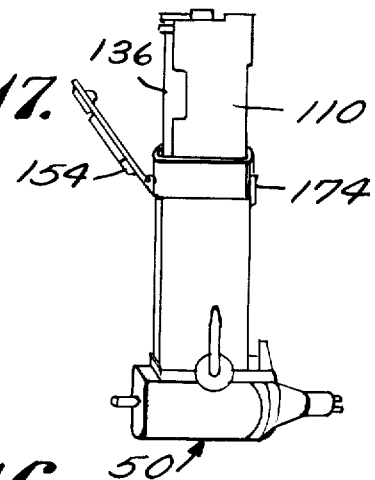
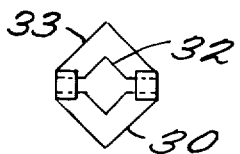
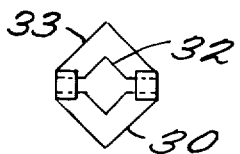
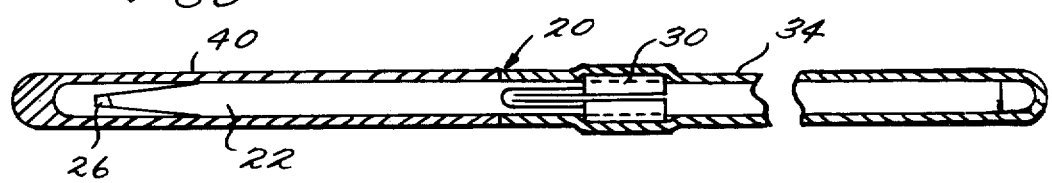
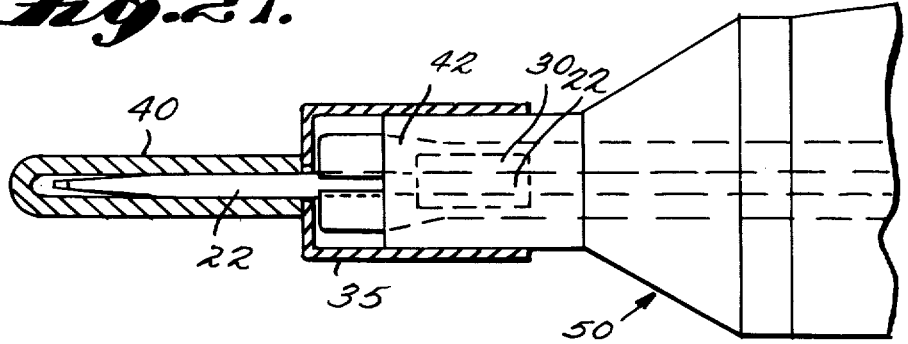

WIRE INSERTER

This is a continuation-in-part of U.S. Pat. application No. 610,869 filed Sept. 5, 1975.

BACKGROUND OF THE INVENTION

The present invention generally pertains to a surgical wire inserter adapted to insert a circular prosthetic device into or through bones to provide support and fixation while the bone structure is mending or to provide anchorage for traction but more particularly pertains to a rotary wire inserting device utilizing a sterile wire pack provided with flats to provide an anti rotational key.

In the prior art a prosthetic wire device usually 3 to 9 inches long and circular in cross section is generally inserted into the bone by means of a pre-drilled hole or more commonly by driving the wire with a suitable drill chuck and letting the wire bore its own hole by means of a spade or trocar tip. A trocar point is the point most commonly used on such wires. One such device which has been used to insert wires is a device called a Loth-Kirschner extension drill. The drill is hand operated with the drill bit being rotated by a suitable gearing which is turned by a handle much like that of a fishing reel.

Another device which has been used is a pneumatic wire driver manufactured by the Stryker Corporation. This device is a hand held device with a trigger. An air supply is connected to the device by way of hoses which pass through the handle of the gun causing the wire to rotate so that it obtains a sufficient torque to be driven into the bone.

Generally speaking the prosthetic wires which are used in both of these instruments and wires which are used in the operating room are circular in cross-section ranging from 0.028 to 0.062 inches in diameter and are primarily provided with a ground spade point or a trocar point. The spade point has a cutting action by virtue of the cutting edges and consequently drills into the bone with relative ease. However, because the spade point drills a hole equal in diameter to the wire, the wire is relatively loose when it is inserted. The trocar point has more of a spreading action rather than a cutting action and therefore drills with relative difficulty which results in a tightly held wire when installed since it does not drill a clearance hole for the wire.

Because of the circular cross section and small diameter of these wires they are difficult to hold in a chuck tightly enough to prevent slipping during installation.

The present invention incorporates a wire having a tip which provides the cutting ease of the spade tip while maintaining the holding properties of the trocar tip. Furthermore, the invention provides anti rotational features on the wire which eliminate the rotational slippage of the wire in the drill chuck during installation. The novel instrument which is used to rotate the wire contains a removable drive cassette carrying a motor and battery power source adapted to selectively rotate the wire. The wire inserter instrument is designed to utilize a prosthetic wire of a substantially circular cross section having one or more flats or grooves to provide anti rotational keying with the chuck which is used for installation.. The wire is constructed with a spade tip specifically designed to cut a hole in the bone smaler in diameter than the major diameter of the wire so that the cutting action of the spade tip is realized while retaining a tight fit between the bone and the wire. This cutting action is achieved by restricting the cutting edges of a conventional spade point to a width less than the wire diameter. The novel wire thus achieves the desired functions of the previously described wire but is more easily gripped and installed than those prior art wires. Thus the wire combines the drilling ease of the spade point with the holding properties of the trocar point. Since the wire is more easily installed requiring less pressure and force to implant in the bone it results in an easier and more accurate installation than conventionally used wires. The material of construciton of the wire is stainless steel or other medically suitable material.

The above mentioned purposes are more readily apparent when read in conjunction with the following detailed description of the preferred embodiment of the present invention.

BRIEF DESCRIPTION OF THE DRAWINGS

FIG. 1 is a side elevational view partially in section of the drill inserter instrument;

FIG. 2 is a plan view partially in section of the drill instrument shown in FIG. 1;

FIG. 3 is an exploded enlarged view of the cam assembly of the instrument shown in FIG. 1;

FIG. 4 is a sectional side view of the removable cassette including the motor and power source assembly;

FIG. 10 is a top end plan view of the cassette shown in FIG. 4;

FIG. 11 is a bottom end plan view of the cassette shown in FIG. 4;

FIG. 12 is an enlarged side view of the tip of the novel prosthetic wire used in the invention;

FIG. 13 is a top plan view of the tip shown in FIG. 12;

FIG. 14 is an enlarged frontal view of the tip of the wire shown in FIG. 12;

FIG. 15 is an elevated side view and frontal view of the prior art wire tip;

FIG. 16 is a side view in section of an enlarged view of the wire capsule assembly which can be used in the invention;

FIG. 17 is an enlarged view of the chuck shown in FIG. 16;

FIG. 18 is an enlarged top plan view of the chuck shown in FIG. 16;

FIG. 19 is a front elevational view of the chuck shown in FIG. 17;

FIG. 20 is a rear elevational view of the chuck shown in FIG. 17;

FIG. 21 is an enlarged cross sectional view of the wire capsule assembly held in the wire inserter instrument; and FIG. 22 is a perspective view showing insertion of the cassette into the wire inserter instrument.

DETAILED DESCRIPTION OF THE EMBODIMENT

Figure 5:
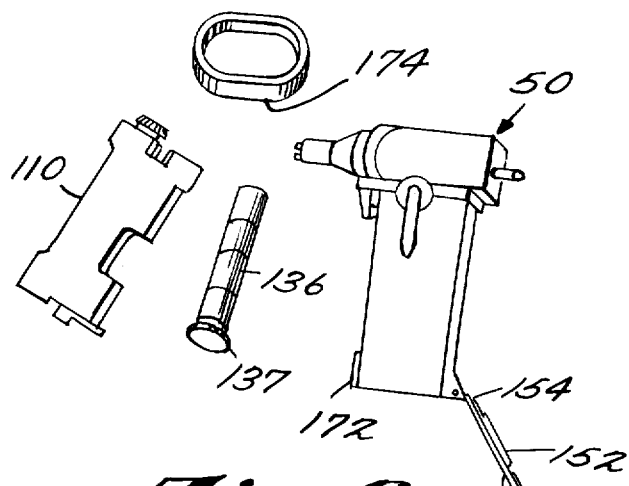
FIG. 5 is an exploded view of the drill inserter instrument, cassette, battery and cassette insertion funnel.

The present invention as shown in FIGS. 1-22 concerns a specially designed wire and tip which is utilized in a unique surgical drill to provide an improved surgical instrument. In the invention a wire assembly 20 which has previously been sterilized in ethylene oxide gas is adapted to be handled and installed in a chuck without contaminating the wire. The sterile assembly 20 is intended to be disposable so that a pre-sterilized encapsulated wire can be used in a non-sterile or sterile wire insertion machine without causing contamination of the wire. Once the wire has been used the remaining portion of the wire is discarded. The wire which is used in the assembly preferably is formed with four flats formed as chords each subtending a center angle of 45° located in an equally spaced manner around the circumference. These flats 24 provide anti rotational keying with the chuck in the machine inserter. The tip of the wire 26 is designed to cut a hole in the bone smaller in diameter than the major diameter of the wire. This result is achieved by orienting a spade point construction approximately normal to the opposite flats 24 on the wire body 22. In this manner the length of the spade cutting tip 26 is restricted to about 92% of the major diameter of the wire body 22. The spade point of the tip allows the wire to be more easily drilled into the bone. A small inner chuck 30 is mounted on the wire. The chuck 30 is constructed with internal flats 32 designed to prevent slippage of the chuck on the wire, and external flats 33 designed to prevent slippage of the chuck 30 within the machine chuck 42. In one embodiment of the wire assembly a thin walled plastic or paper sleeve 34 emcompasses the inner chuck and most of the wire length. A plastic or paper cap 40 encloses the wire tip extending in front of the inner chuck to keep it in a sterilized condition.

In use the wire assembly 20 is inserted into a chuck 42 of the surgical instrument 50 used for wire insertion as is shown in FIG. 21. The chuck 42 of the insertion instrument is tightened into the inner chuck 30 of the capsule assembly through the plastic or paper sleeve 34. The inner chuck in turn grips the wire body 22 so that once it is installed in a tightened chuck of the instrument, the cap 40 is removed exposing the tip of the sterile wire which is ready for use. The sterile cap 35 which goes over the end of the chuck can be constructed to protect further against contamination. While the cap and the sleeve or wall of the capsule assembly are preferably constructed of plastic it should be noted that paper can be substituted if such is desired. The wire itself is preferably constructed of stainless steel or other medically suitable non-toxic material which can be safely inserted into the bone structure or other parts of the body.

While the anti rotational features of the wire 22 and the inner chuck 30 are preferably flats, 24, 32 and 33, it should be noted that other anti rotational features such as teeth, grooves, or keys can be substituted if desired.

Figure 9:
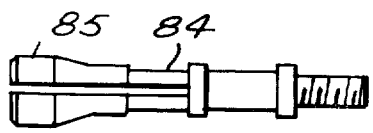
FIG. 9 is a side elevational view of the collet shown in FIG. 6.
Figure 7:
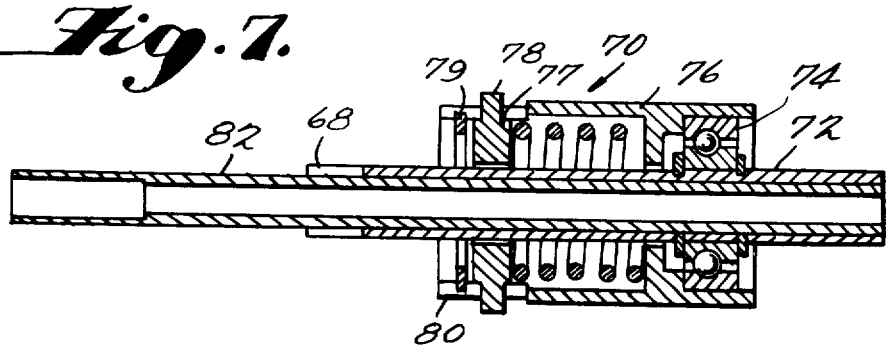
FIG. 7 is an enlarged cross section of the draw tube cartridge assembly of the invention.

The instrument 50 which operates and holds the prosthetic wire comprises an external casing 52 consisting of a handle housing 53, a wire drive housing 54 and a nose housing 56. A split collet 84 as shown in FIG. 9 is mounted in a collet tube 58 positioned in the nose housing 56 of the instrument and functions as the instrument chuck. The collet tube 58 is retained in a bearing assembly 60 which is mounted in the nose housing 56. The collet tube 58 is further supported by a nylon bushing 62. The front of the collet tube 58 is tapered inwardly forming an inner conical surface 63 to receive the conical shaped section 64 of the split collet member 84. The rear of the collet tube 66 is connected by a spline arrangement 68 to draw tube assembly 70 as shown in FIG. 1. The draw tube assembly 70 comprises a draw tube 72 retained in a ball bearing assembly 74 which is in turn retained in a piston 76. A thrust ring 77 is free to move laterally in the piston and is limited in movement by the piston casing and a retaining ring 79 mounted in the piston casing. Pins 78 extend from the thrust ring and ride in grooves 80 to prevent rotation of the thrust ring. An inner draw tube 82 which is secured to the draw tube 72 extends forward inside the collet tube 58 to a point where it is attached to a split collet 84. The split collet 84 has an external conical section 64 which mates with the inner conical surface of the collet tube 58. Thus when the draw tube assembly 70 is moved in rearward direction, the conical portion 64 of the collet is pulled into the conical portion of the collet tube causing the jaws 85 of the split collet 84 to close.

An operating lever 94 mounted to one end of cam rod 88 extends downwardly alongside the instrument handle. The cam rod 88 extends across and through the drive housing. Two thrust bars 90 and 92 are located on either side of the piston 76 inside the drive housing and are provided with planar cutouts which bear against flats 89 formed on the cam rod 88 so that when the cam rod is rotated 90° by turning the lever 94 the thrust bars move rearwardly and apply pressure to pins 78 extending from the thrust ring 77. The pressure on the thrust ring is transmitted to the piston by means of a spring 98. When the operating lever 94 is rotated 90° the thrust bars cam against the pins, the thrust ring and spring to move the piston rearward. This movement moves the draw tube rearwardly causing the collet jaws to close which tightens the inner chuck 30 of the capsule assembly and grips the wire 22 as previously described. The holding force of the collet jaws is determined by the spring strength in the piston which limits the draw force and prevents overstressing of the instrument parts. Another spring 100 is located behind the piston and acts to return the piston and the draw tube assembly to its forward position when the lever 94 is returned to its original position. In this manner the grip of the collet jaws is released and the wire is free to slip in or out of the instrument. Rotary motion is applied to the collet tube 58, draw tube 72 and split collet 84 through a bevel gear 102 secured to the collet tube 58. This gear is driven by a mating bevel gear 104 connected to a drive shaft 106 mounted on an electric motor 108. The electric motor 108 is solely housed within a cassette 110 along with its power source 112.

The electric motor 108 and power source 112 are mounted in chambers 109 and 113 formed in the plastic cassette body 114. A switch assembly 116 is positioned in the top portion of the cassette body next to the bevel gear 104. The switch assembly 116 comprises an angular shaped transmitting piece 118 which is slotted at 120 to allow the drive shaft 106 to extend there through. This transmitting piece 118 is engaged by trigger 122 positioned outside the handle and drives against a U-shaped slide 124 which in turn engages a micro switch 126. The micro switch 126 is held in position by a screw 128 which extends through a part of the cassette housing and terminates against an electrical contact 130 which is in turn spaced by a washer 132.

Figure 8:
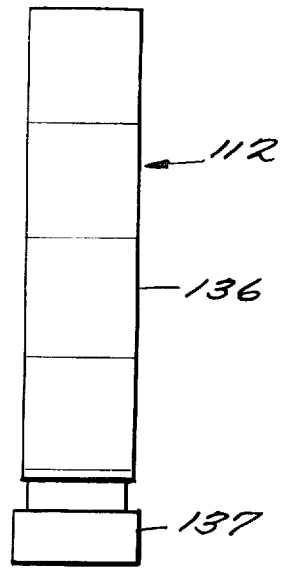
FIG. 8 is an enlarged view of the battery pack assembly of the invention.
Figure 6:
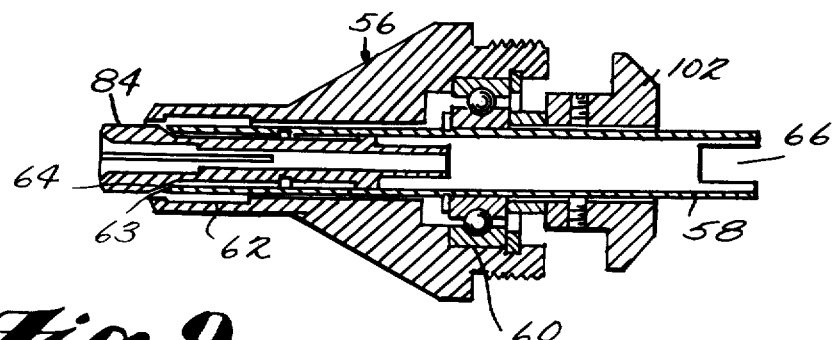
FIG. 6 is an enlarged cross sectional view of the nose collet assembly of the invention shown in FIG. 2.

In operation, trigger 122 is pulled back towards the handle moving the transmitting piece 118 against slide 124 which activates the micro switch 126. The small button 127 of the micro switch is a button switch which is depressed when slide 124 engages it energizing the motor. The battery chamber 109 defined by the cassette housing contains an assembly adapted to hold a battery pack 136. The battery pack engages a spring 138 and contacts connecting lug 140 for an electrical connection. Positioned below the motor 108 in the motor chamber 113 is a switch assembly 142 containing the forward and reverse rotation switches. In the assembly a teeter totter member 144 is held by a pivoting pin 146 so that the arms 148 and 150 of the teeter totter form two switches, one for forward and one for reverse. A small formed flat spring rides on the top of the teeter totter member to engage micro switches as the arms are depressed. When the arm to the right is depressed the motor is placed in reverse phase but when the arm is depressed to the left the motor is placed in a forward phase. The motor drive and consequent teeter totter arm depression is accomplished by a surrated round sliding switch 152 which is slidably mounted on the hinged cap 154 of the handle. FIG. 8 shows the battery pack of the cassette. Spring 160 in the switch assembly has its ends brought up into a modified U-shape to engage the bottom cap 154 of the handle and force the cassette 110 upward so that the gears engage properly when the cap 154 is latched on the handle. This spring is held in place by a screw 162 mounted upon washer 164. The motor 108 that is preferably used in the invention is a 6 volt 8400 RPM 0.72 oz. inch per amp. commonly known by the trade as a MIRCOMO.

The battery pack 136 is provided on one end with a stop ring 137 which permits the battery pack to be loaded into the cassette in only one direction thus assuring correct loading of the cassette.

It can thus be seen by the invention that the handle cap 154 can be released from the latch mechanism 172 on the handle so that the cassette 110 can be removed from the handle. This removal allows either a new battery pack to be placed in the cassette or allows the instrument 50 to be autoclaved for sterile instrument usage. Thus it can be seen that the instrument can be autoclaved in a conventional manner such as by heat and or steam with no damage to the battery or to the motor. In addition, the cassette 110 can be easily loaded in the handle through the use of the funnel shaped ring 174 as is shown in FIG. 22. As shown in FIG. 22 the instrument 50 is turned up side down and the handle cap 154 opened. The ring 174 mounted on the handle base and the cassette 110 is dropped in the handle in an aligned position.

The funnel shaped ring 154 is preferably constructed of aluminum and the instrument housing is aluminum. The moving parts are preferably constructed of steel.

While the preferred embodiment of the invention has been disclosed, it is understood that the invention is not limited to such an embodiment since it may be otherwise embodied in the scope of the appended claims.

What is claimed is:

1. A portable surgical wire inserting instrument comprising a housing, said housing defining a handle and a drive casing, a removable cassette comprising motor means, switch means and a source of electrical power, mounted in said housing and completely enclosed within said housing handle, said motor means mounted in said cassette, said electrical source of power mounted in said cassette and adapted to power said motor means when electrically connected to said motor means by said cassette switch means enclosed within said cassette, a wire holding tube means mounted in said housing, said wire holding tube means being provided with chuck means at one end, the chuck means being adapted to grab and hold a wire inserted in said wire holding tube in a fixed position, gear means connecting said motor means to said wire holding tube means adapted to rotate said wire holding tube means and external switch means movably mounted on said housing, said external switch means being connected to said cassette switch means and adapted to engage said cassette switch means to engage said motor means.

2. An instrument as claimed in claim 1 wherein said source of power is a battery.

3. An instrument as claimed in claim 1 wherein said cassette has an exterior configuration the same as the interior configuration of the handle housing.

4. An instrument as claimed in claim 1 including gear means mounted exterior of said cassette and connected to said motor means by a drive shaft.

5. An instrument as claimed in claim 1 including a rechargeable battery pack mounted in said cassette, said battery pack being held in place in said cassette by spring means.

6. An instrument as claimed in claim 1 including a second switch means mounted on said cassette adapted to selectively place said motor in opposite rotational phase.

7. A portable surgical wire inserting instrument comprising a housing, said housing defining a handle and a drive casing, a removable cassette slidably mounted within said handle and contained therein so that the cassette is not exposed to contamination from outside environment during a surgical operation, a motor means mounted to and carried by said removable cassette, a removable battery pack electrically connected to said motor means and removably mounted in said cassette, a wire holding means mounted in said drive casing, said wire holding means being provided with chuck means at one end, the chuck means being adapted to grab and hold a wire inserted in said wire holding means in a fixed position, gear means connecting said motor means to said wire holding means, said gear means being adapted to rotate said wire holding means and switch means mounted on said cassette, said switch means being adapted to energize said motor means when engaged by a trigger mechanism mounted on said housing.

8. An instrument as claimed in claim 7 including a second switch means mounted on said cassette adapted to selectively place said motor in opposite rotational phases.

9. A instrument as claimed in claim 8 wherein said second switch means comprises a sliding member mounted in said handle and a teeter totter switch mounted on said cassette adjacent said sliding member and adapted to be engaged by said sliding member contacting micro switch means mounted in said cassette and reverse the rotation of a drive shaft mounted in said motor.

10. A portable surgical wire inserting instrument comprising a housing, said housing defining a handle and a drive casing, a removable cassette slidably mounted within said handle, a motor means mounted in said removable cassette, a removable battery pack electrically connected to said motor means and mounted in said cassette, a wire holding means mounted in said drive casing, said wire holding means being provided with chuck means at one end, the chuck means being adapted to grab and hold a wire inserted in said wire holding means in a fixed position, gear means connecting said motor means to said wire holding means, said gear means being adapted to rotate said wire holding means and switch means mounted on said cassette, said switch means being adapted to energize said motor means when engaged by a trigger mechanism mounted on said housing wherein said switch means comprises a first sliding member mounted on said cassette, a second sliding member mounted on said cassette adjacent said first sliding member and a micro switch mounted on said cassette adjacent said second sliding member, said trigger member when moved engaging said first sliding member which forces said second sliding member into said micro switch energizing said motor.

11. An instrument as claimed in claim 7 including a latch means secured to said handle and a handle cap fastened to said latch means.

12. An instrument as claimed in claim 7 including a cap removably mounted to the end of said handle.

13. An instrument as claimed in claim 7 wherein said battery pack is provided with a member mounted on one end which is of greater diameter than the diameter of the battery pack body.

14. A portable surgical wire inserting apparatus comprising in combination a housing, said housing defining a handle, a drive casing and a nose piece removably mounted to said drive casing, a removable cassette slidably mounted in said handle, said cassette being totally isolated from the external environment by said housing when said cassette is inserted into said housing, a motor means mounted in and carried by said cassette; a source of power mounted in said cassette and connected to said motor means, a wire holding tube means mounted in said housing, said wire holding tube means being provided with chuck means at one end, a wire pack inserted in said wire holding tube means, said wire pack comprising a substantially circular wire, an inner chuck mounted on said wire to prevent slippage of said wire in chuck means, the chuck means being adapted to hold and apply pressure to said inner chuck inserted in said wire holding tube, gear means carried by said cassette connecting said motor means to said wire holding tube means adapted to rotate said wire holding tube means and switch means mounted to said housing, said switch means being adapted to energize said motor causing said gear means to rotate.

* * * * *